(12) United States Patent
Kobayashi

(10) Patent No.: US 7,307,193 B2
(45) Date of Patent: Dec. 11, 2007

(54) MICROENCAPSULATED METAL CATALYST

(75) Inventor: Shu Kobayashi, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 500 days.

(21) Appl. No.: 10/469,916

(22) PCT Filed: Feb. 15, 2002

(86) PCT No.: PCT/JP02/01298

§ 371 (c)(1),
(2), (4) Date: Nov. 7, 2003

(87) PCT Pub. No.: WO02/070131

PCT Pub. Date: Sep. 12, 2002

(65) Prior Publication Data

US 2004/0077905 A1   Apr. 22, 2004

(30) Foreign Application Priority Data

Mar. 5, 2001   (JP) ............................. 2001-059742

(51) Int. Cl.
*C07C 43/00* (2006.01)
*B01J 31/00* (2006.01)
*C08F 12/00* (2006.01)

(52) U.S. Cl. ................... 568/687; 502/159; 526/346

(58) Field of Classification Search ................ 502/159; 568/687

See application file for complete search history.

(56) References Cited

U.S. PATENT DOCUMENTS 4,766,176 A   8/1988   Lee et al.

FOREIGN PATENT DOCUMENTS

| EP | 300643 | 1/1989 |
| EP | 940170 | 9/1999 |
| JP | 61-133202 | 6/1986 |

OTHER PUBLICATIONS

Kobayashi et al. Journal of American Chemical Society, 1999, 21, p. 11229-30.*
Trost et al. Journal of American Chemical Society, 1992, 114, p. 8745-8747.*
Ryo Akiyama et al., "Micro Capsule Ka Palladium Shokubai no Kaihatsu", CSJ: The Chemical Society of Japan Koen Yoki Shu, vol. 79, No. 2, p. 1141, Mar. 15, 2001.
Ryo Akiyama et al., "Microencapsulated Palladium Catalysts: Allylic Substitution and Suzuki Coupling Using a Recoverable and Reusable Polymer-Supported Palladium Catalyst", Angew. Chem., Int. Ed. Engl., vol. 40, No. 18, pp. 3469-3471, Sep. 17, 2001.

* cited by examiner

*Primary Examiner*—Rebecca Anderson
*Assistant Examiner*—Yong Chu
(74) *Attorney, Agent, or Firm*—Wenderoth, Lind & Ponack, L.L.P.

(57) ABSTRACT

A microencapsulated Group VIII metal catalyst which is stable even in air, easy to recover, and reusable is disclosed. It comprises a polymer with side chains containing an aromatic substituent, and a metal catalyst comprising a Group VIII metal encapsulated in to this polymer.

5 Claims, No Drawings

MICROENCAPSULATED METAL CATALYST

TECHNICAL FIELD

The invention of the present application relates to a microencapsulated metal catalyst. More particularly, the invention of the present application relates to a microencapsulated metal catalyst that is applicable to various organic synthesis reactions, stable in air, and reusable.

BACKGROUND ART

Metal catalysts comprising Group VIII metals such as iron (Fe), cobalt (Co), ruthenium (Ru), rhodium (Rh), palladium (Pd). platinum (Pt) are known as useful catalyst systems because they are capable of causing various transformation reactions in organic synthesis. However, such Group VIII metal catalysts have various disadvantages in that they are costly, deteriorate when in contact with air impossible to regenerate, etc. In order to solve such problems, immobilization of catalysts has been studied and many reports on various polymer-immobilized metal catalysts have been published. For example, polymer-immobilized metal catalysts that are effective for allylic substitution (*J. Am. Chem. Soc.* 1978, 100. 7779; *J. Org. Chem.* 1983, 48. 4179 and others). oligomerization (*J. Org. Chem.* 1989, 54, 2726; *J. Catal.* 1976, 44, 87; *J. Organomet. Chem.* 1978, 153. 85 and others), decarboxylation (*J. Mol. Catal.* 1992. 74, 409), hydrogenation (*Inorg. Chem.* 1973, 12, 1465 and others), isomerization (*J. Org. Chem.* 1978, 43, 2958 and others), telomerization (*J. Org. Chem.* 1981, 46, 2356), and Mizoroki-Heck reaction (*Fundam. Res. Homogeneous Catal.* 1973, 3, 671; *J. Organomet. Chem.* 1978, 162, 403 and others), etc, have been reported.

However, although the stability of the catalyst was improved by their immobilization in polymer, the recovery and reuse of the polymer-immobilized metal catalyst have been unsatisfactory for such known catalyst systems.

Therefore, the invention of the present application has been achieved in consideration of the above-mentioned situation, and aims to solve the problems of the conventional techniques by providing a novel Group VIII metal catalyst system that is stable even in air, easy to recover, and reusable.

DISCLOSURE OF THE INVENTION

As a catalyst to solve the above-mentioned problems, the invention of the present application provides firstly a microencapsulated metal catalyst, which comprises a metal catalyst containing a Group VIII metal encapsulated in a polymer that has side chains containing an aromatic substituent.

Secondly, the invention of the present application provides the microencapsulated metal catalyst of claim 1, wherein the polymer that has side chains containing an aromatic substituent is a polymer having styrene units; and thirdly, the invention provides the above-described microencapsulated metal catalyst, wherein the metal catalyst is a triphenylphosphine metal catalyst represented by the following general formula (I):

$$M(PPh_3) \qquad (I)$$

(wherein M represents a Group VIII metal).

Further, fourthly, the invention of the present application provides any of the above-described microencapsulated metal catalyst, wherein the Group VIII metal is at least one metal selected from the group consisting of palladium, rhodium, ruthenium, iridium, and platinum.

Fifthly, the invention of the present application provides a method for allylation reaction, which comprises reacting a C-nucleophile and an allylic carbonate in the presence of any of the above-mentioned microencapsulated metal catalyst; sixthly, the invention provides a method for allylation reaction, which comprises reacting a C-nucleophile and an allyl acetate in the presence of any of the above-described microencapsulated metal catalyst, and seventhly, the invention provides a method for coupling reaction, which comprises reacting a boric acid compound and an aryl bromide in the presence of any of the above-described microencapsulated metal catalyst.

Further, eighthly, the invention of the present application provides any of the methods for reaction .described as the fifth, sixth, and seventh aspects of the present invention, wherein the reaction is performed in the presence of the microencapsulated metal catalyst and an external ligand.

Finally, ninthly, the invention of the present application provides a method for asymmetric synthesis reaction, which comprises reacting a C-nucleophile and an allylic carbonate in the presence of any of the above microencapsulated metal catalyst and a chiral ligand.

BEST MODE FOR CARRYING OUT THE INVENTION

The inventors of the present invention have previously reported microencapsulated scandium methanesulfonate (MC Sc(OTf)$_3$) (*J. Am. Chem. Soc.* 1998, 120, 2985) and microencapsulated osmium tetraoxide (MC OsO$_4$) (*J. Org. Chem.* 1998, 63, 6094; *J. Am. Chem. Soc.* 1999, 121, 11229) as polymer-immobilized metal catalysts that are completely different from those previously reported. These catalyst systems were obtained by immobilizing catalysts in polymers through interactions between the π electrons of the aromatic substituents present in the polymer side chains and the vacant electron orbitals of the catalyst. The inventors have further investigated the immobilization of catalysts containing metals of an entirely different atomic structure and oxidized state from those of Sc and Os, Group VIII metal catalysts in particular, to a polymer by a similar mechanism, and achieved the invention of the present application.

That is, in the microencapsulated metal catalyst of the present invention, the metal catalyst containing a Group VIII metal is encapsulated in a polymer that has side chains containing an aromatic substituent, and thus does not deteriorate easily by air or water and is easy to recover and reuse.

In the microencapsulated metal catalyst of the present invention, the polymer with side chains containing an aromatic substituent may be any polymer and the structure of the main chain and side chains, stereoregularity, molecular weight, and the like are not particularly limited. Any polymer that generally does not inhibit the encapsulation of the metal catalyst, that is also capable of forming a microcapsule structure may be used. Polymers that contain a phenyl group in its side chain are preferable and more preferable are those polymers that contain polystyrene units. Such polymers may be polystyrene homopolymer, copolymers of styrene unit and one or more types of other monomer units, or mixed polymers of polystyrene and other homopolymers or copolymers. Of course, the above-mentioned phenyl group may contain an appropriate organic group.

Further, in the microencapsulated metal catalyst of the present invention, the metal catalyst is not particularly limited and may be any catalyst as long as it contains a Group VIII metal; that is, iron (Fe), ruthenium (Ru), osmium (Os), cobalt (Co), rhodium (Rh), iridium (Ir), nickel (Ni), palladium (Pd), or platinum (Pt) These metal catalysts may be in the form of various metal compounds such as complex compounds, organometallic compounds, inorganic salts, or organic salts. As the complex compounds, olefin type complexes comprising olefin or diolefin with metals, phosphine type complexes comprising phosphine or diphosphinoethane with metals, amine type, complexes comprising amine, diumine, piperidine, and the like with metals Preferable is a triphenylphospbine metal catalyst represented by the following general formula (I):

$$M(PPh_3) \tag{I}$$

(wherein M represents a group VIII metal). In this case, the phenyl group comprising the triphenylphosphine may contain various allowable organic groups. Many reports have been made on the effect of such triphenylphosphine metal catalysts on various organic synthesis reactions.

Further, in the microencapsulated metal catalyst, the above-mentioned Group VIII metal may be any metal as described above, but ruthenium (RU), palladium (Pd), and platinum (Pt) are particularly preferable.

The above-described microencapsulated metal catalyst may be any one as long as a Group VIII metal is encapsulated in a polymer with side chains containing an aromatic substituent, and its production method is not limited various techniques studied and reported in the fields of medicine and pharmaceutics may be employed; specifically, the inventors and their co-workers have previously reported (J. Am. Chem. Soc. 1998. 120, 2985) that a known method for obtaining microcapsules by dissolving a metal catalyst in a solution of the polymer with side chains containing an aromatic substituent, stirring and cooling the resulting solution, and adding a poor solvent of the polymer in which the metal catalyst is dispersed and introduced, and curing the swollen polymer (Microcapsules and Nanoparticles in Medicine and Pharmacy; CRC Press: Boca Raton, 1992) is applicable.

Further, in the microencapsulated metal catalyst of the present invention, the metal catalyst may be enclosed in the polymer in any form. For example, the metal catalyst may be physically enclosed in a polymer capsule, or may be immobilized by the electronic interactions between the main chain, side chain or substituents of the polymer and the metal. Presumably, the Group VIII metal catalyst is physically enclosed by the polymer and is, at the same time, immobilized by interactions between the π electrons of the aromatic substitutents of the polymer side chain and the vacant electron orbitals of the Group VIII metal catalyst (J. Am. Chem. Soc. 1998, 120, 2985).

The present invention also provides various chemical reactions that uses the above-described microencapsulated metal catalyst. Specifically, a method for allylation reaction and asymmetric synthesis reaction, which comprises reacting a C-nucleophile and an allylic carbonate, a method for allylation reaction, which comprises reacting a C-nucleophile and an allyl acetate, and a method for coupling reaction, which comprises reacting a boric acid compound and an aryl bromide, may be exemplified.

In the allylation reaction, an allylation product may be obtained by reacting an ally carbonate represented by the following general formula (II):

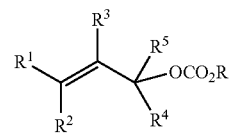
(II)

(wherein R represents an alkyl group, $R^1$ to $R^5$ each represent a hydrogen atom or a hydrocarbon group that may contain a substituent) with a β-ketoester in the presence of the microencapsulated metal catalyst of the present invention. Here, the type of solvent used is not limited and an appropriate solvent that can dissolve the starting substance may be selected from various organic solvents. Further, in the reaction, the amount of the microencapsulated metal catalyst may be selected taking in to account the amounts and concentrations of the starting substances and is thus not particularly limited. Preferably, the amount of the microencapsulated metal catalyst is 0.01 to 0.5 mmol.

Such allylation reaction is especially promoted in the presence of an external ligand, and result in high yield of the product. Here, the external ligand to be added is not limited but it is preferable to use a ligand identical to that of the Group VIII metal catalyst enclosed in the polymer on the other hand, when the external ligand is a chiral ligand, a highly enantioselective asymmetric synthesis is promoted by reacting an allylic carbonate and a β-ketoester. The amount of the external ligand is not particularly limited: however, it is preferable to adjust its molar amount to ½ to 2 times that of the microencapsulated metal catalyst, since under such conditions the yield of the product and the recovery percentage of the microencapsulated metal catalyst becomes high.

On the other hand, in the allylation reaction of ally acetate, allylation occurs by reacting an ally acetate represented by, for example, the following general formula (III):

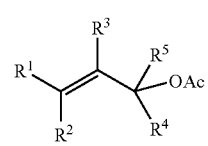
(III)

(wherein $R^1$ to $R^5$ each represent a hydrogen atom or a hydrocarbon group that may contain a substituent) and a ketoester in the presence of the microencapsulated metal catalyst of the present invention. Here, the type of the solvent to be used and the amount of the microencapsulated metal catalyst are as described above. Further, in such allylation reaction, as with the above-described allylation reaction, the coexistence of an external ligand further improves the yield of the product. In this case, the external ligand to be added may be any ligand, but it is preferable to use a ligand identical to that of the Group VIII metal catalyst enclosed in the polymer. It is also preferable that the amount of the external ligand is as described above. Further, in order to promote the reaction, in such allylation, a substance other than the starting substances and the microencapsulated metal catalyst, such as an acid, base or organic salt, may be added.

Further, the microencapsulated metal catalyst of the present invention enables the promotion of a coupling reaction. Coupling occurs in high yield by reacting a boric acid compound represented by the following general formula (IV):

R'B(OH)$_2$ (IV)

(wherein R' represents a hydrocarbon group that may contain a substituent) and an aryl bromide in the presence of the microencapsulated metal catalyst. In such coupling reaction, the type of solvent to be used and the amount of microencapsulated metal catalyst are as described above. Furthermore, in such coupling reaction, as with the foregoing allylation reaction, coexistence of an external ligand further improves the yield of the product. In this case, the external ligand to be added may be any ligand and tri-o-tolylphosphine and the like may be exemplified. As in the foregoing reactions, the amount of the external ligand is not particularly limited; however the molar amount is preferably ½ to 2 times that of the microencapsulated metal catalyst.

Hereinafter, embodiments of the invention will be described in further detail with reference to the following Examples. Of course, the invention is not limited to the following Examples and various embodiments are possible.

EXAMPLES

Example 1

Method for Producing Microencapsulated Triphenylphosphine Palladium Catalyst (MC Pd(PPh$_3$))

Polystyrene (1.000 g) was dissolved in cyclohexene (20 mL) at 40° C., and to this solution, tetrakis (triphenyl phosphine) palladium(O) (Pd(PPh3)$_4$, 0.20 g) was added and dissolved as a core. The resulting solution was stirred for 1 h at the same temperature until the color of the mixture changed from brown to black. The solution was slowly cooled to 0° C., which resulted in the envelopment of the dispersed core by the polymer, and phase separation was observed.

Further, hexane (30 mL) was added to harden the capsule walls. The solution was further left at room temperature for 12 h, after which the capsules were washed several times with acetonitrile and dried at room temperature for 24 h. Three equivalents of triphenylphosphine (PPh$_3$) were recovered by washing and one equivalent of PPh$_3$ remained in the microcapsules.

Only one peak was observed for the PPh$_3$ coordinated on palladium by $^{31}$P Swollen-Resin Magic Angle Spinning (SR-MAS) NMR of the catalyst-containing microcapsules. Accordingly, it was speculated that the catalyst was encapsulated as Pd(PPh3).

The validity of the analysis method by SR-MAS NMR, which enables the direct analysis of the resin structure without separating the metal from the polymer carrier, has been proven through various solid-phase reactions using cross-linked polystyrene-type resins developed by the inventors (*Mol. Online* 1998, 2, 35; *Tetrahedron Lett.* 1998, 39, 7345; *Tetrahedron Lett.* 1998. 39, 9211; *Tetrahedron Lett.* 1999, 40, 1341; *J. Comb. Chem.* 1999, 1, 371; *Heterocycles* 2000, 52, 1143; *H. Comb. Chem.* 2000, 2, 438).

Example 2

Allylation Reaction Using MC Pd(PPh$_3$)

Using the MC Pd(PPh$_3$) obtained in Example 1, allyl methyl carbonate (compound 1) and dimethyl phenylmalonate (compound 2) were reacted in accordance with the following chemical formula (A).

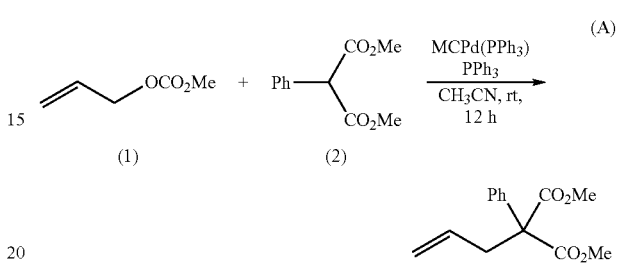

When 20 mol % of MC Pd(PPh$_3$) alone was added, the reaction did not proceed. However, when PPh$_3$ was added as an external ligand, the reaction proceeded smoothly.

Similar reactions were carried out with various PPh$_3$ and the reaction was repeated using catalyst. The results are shown in Table 1.

TABLE 1

| MC Pd (PPh$_3$) | PPh$_3$ | yield (catalyst recovery ratio) % | | |
|---|---|---|---|---|
| mol % | mol % | 1st | 2nd | 3rd |
| 20 | 0 | 0 | — | — |
| 20 | 10 | 94 (quant) | 61 (99) | 30 (99) |
| 20 | 20 | 83 (quant) | 90 (quant) | 84 (quant)* |
| 20 | 40 | 92 (quant) | 81 (99) | 77 (quant) |

*4th: 94 (quant), 5th: 83 (quant)

From the table, it was found that when 20 mol % of external ligand (PPh$_3$) was used, the product was obtained in a yield as high as that of the first reaction, even after the catalyst was recovered and reused five times.

Example 3

Allylation Reactions of C-Nucleophiles with Allylic Carbonates Using MC Pd(PPh$_3$)

Compound 1 (0.55 5 mmol), compound (0.5 mmol), PPh$_3$ (0.1 mmol), and MCPd(PPh$_3$) (0.1 mmol. 20 mol %) were mixed in acetonitrile (5 mL), and stirred at room temperature for 12 h. After ethanol was added to quench the reaction. MC Pd(PPh$_3$) was filtered and washed with ethanol and acetonitrile and dried. The filtrate was removed in vacuum and the crude product was purified by TLC to obtain the produce in an 83% yield. Further, the recovered MC Pd(PPh$_3$) could be used repeatedly without deterioration of the activity. (Reaction No. 1)

Reactions of various C-nucleophiles with ally carbonates are summarized in Table 2.

TABLE 2

| Reaction number | allylic carbonate | Nucleaphile | Product | Yield (%) |
|---|---|---|---|---|
| 1 | 1 | 2 | Ph, CO₂Me / CO₂Me (allyl) | 83 |
| 2 | 1 | 2-ethoxycarbonyl-1-indanone | 2-allyl-2-ethoxycarbonyl-1-indanone | 86 |
| 3 | 1 | ethyl 2-methyl-3-oxobutanoate | allyl product with OCO₂Et | 60 |
| 4 | (3) 2-methylallyl OCO₂B | 2 | Ph, CO₂Me / CO₂Me (methallyl) | 69 |
| 5 | (4) Ph~~OCO₂B (cinnamyl) | 2 | Ph~~ CO₂Me / CO₂Me | 92 |
| 6 | 4 | ethyl acetoacetate | Ph~~ CO₂Et product | 79 |
| 7 | (5) AcO~~OCO₂Me (Z) | 2 | AcO~~ Ph, CO₂Me / CO₂Me (E) | 64 |

Various malonates and β-ketoesters smoothly reacted to afford the corresponding allylation adducts in high yields. While the reaction of ethyl ac to acetate with (E)-cinnamyl methyl carbonate (compound 4) gave a mixture of E/Z steroisomers (E/Z=64/36) (Reaction No. 6), only E isomers were obtained in the reactions of compound 2 with the compound 4 (Reaction No. 5) and (Z)-carbonate (compound 5) (Reaction No. 7).

The recovery of the catalyst was quantitative in all cases and the recovered catalyst could be reused.

Example 4

Allylation Reaction of Allyl Acetate Using MC Pd (PPh₃)

As shown in the following chemical formula (B), compound 2 shown in the Example 2 was reacted with allyl acetate in the presence of MC Pd(PPh3), PPh3, N,O-bis(trimethylsilyi)acetamide (BSA) and a catalytic amount of potassium acetate, to afford the corresponding adduct in 90% yield.

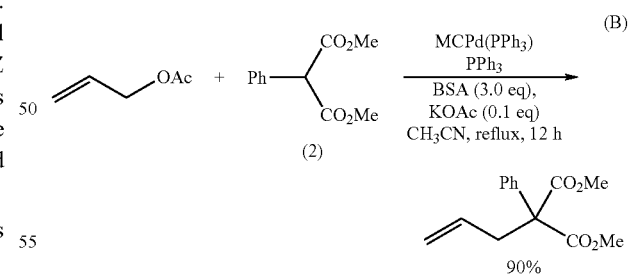

Example 5

Coupling Reaction Using MC Pd(PPh₃)

Various boric acid compounds were reacted with various aryl bromides in the presence of MC Pd(PPh₃) to afford products in high yields as shown in chemical formulas (C) and (D).

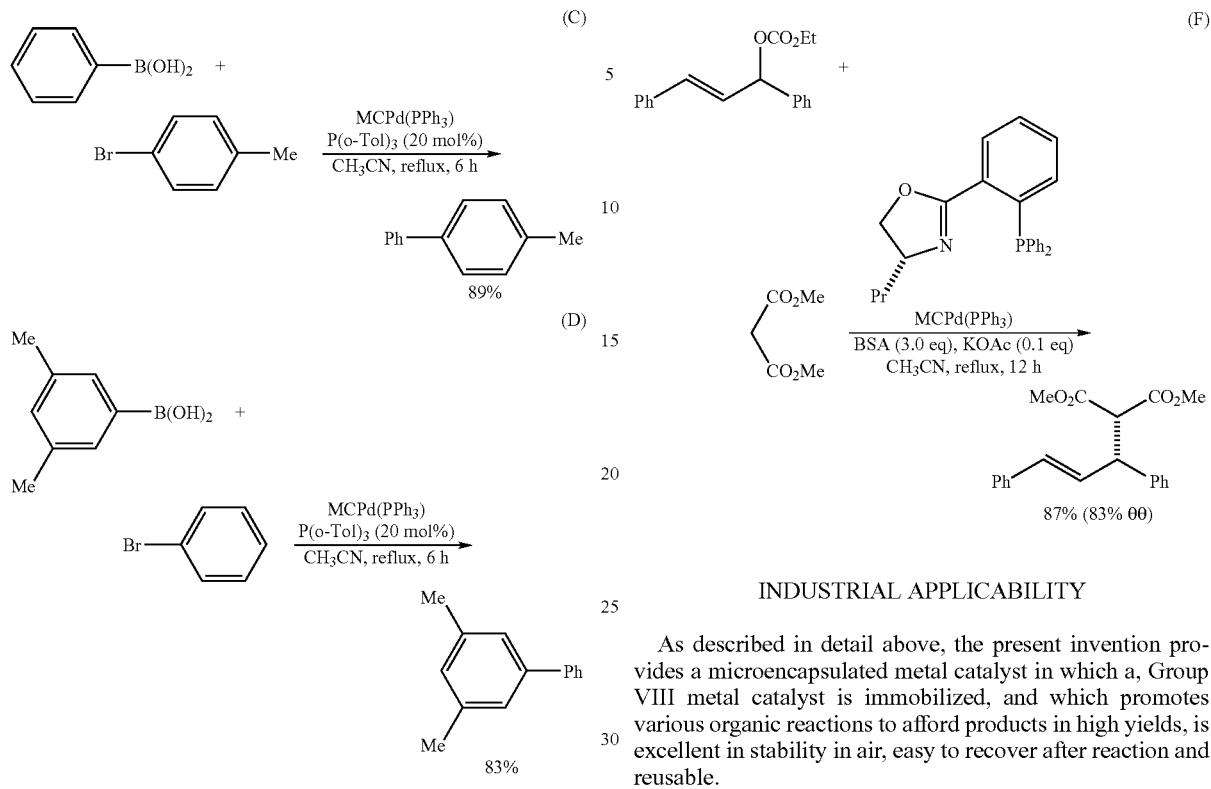

Further, as shown in the following chemical formula (E), when 2-bromothiophene was used instead of aryl bromide, the reaction proceeded to provide a product in high yield.

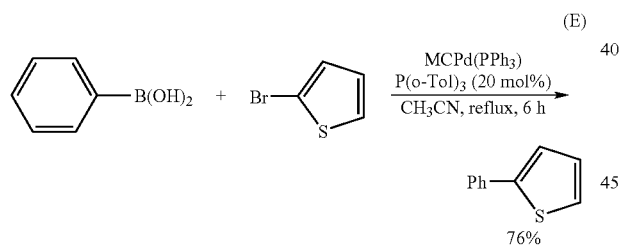

In these coupling reactions, by using tri-o-tolylphosphine (P(o-Tol)₃) as the external ligand, high yield and recovery percentage of MC Pd(PPh3) was obtained.

Example 6

Asymmetric Synthetic Reaction Using MC Pd(PPh₃)

As shown in the following chemical formula (F), 1,3-diphenyl-2-propen-1-yl ethyl carbonate (1.0 equiv.) and dimethyl malonate (3.0 equiv.) were reacted in the presence of MC Pd(PPh₃) (20 mol %), 2-(o-diphenylphosphinophenyl)-(4R)-isopropyloxazoline (20 mol %), BSA (3.0 equiv.), and potassium acetate (0.1 equiv.) under reflux conditions in acetonitrile, to obtain a product in 87% yield with an optical purity of 83% e.

INDUSTRIAL APPLICABILITY

As described in detail above, the present invention provides a microencapsulated metal catalyst in which a, Group VIII metal catalyst is immobilized, and which promotes various organic reactions to afford products in high yields, is excellent in stability in air, easy to recover after reaction and reusable.

The invention claimed is:

1. A method for allylation reaction, which comprises reacting a C-nucleophile and an allylic carbonate in the presence of a microencapsulated metal catalyst in which a metal catalyst containing palladium is encapsulated in a polymer that has side chains containing an aromatic substituent,
   wherein the metal catalyst is a triphenylphosphine metal catalyst represented by the following general formula (I);

M(PPh₃)                    (I)

wherein M represents palladiunm.

2. The method of claim 1, wherein the reaction is performed in the presence of the microrncapsulated triphenyiphosphine metal catalyst Pd(PPh₃) and an external ligand.

3. A method for asymmetric synthesis reaction, which comprises reacting a C-nucleophile and an allylic carbonate in the presence of a microencapsulated metal catalyst in which a metal catalyst containing palladium is encapsulated in a polymer that has side chains containing an aromatic substituent, and a chiral ligand,
   wherein the metal catalyst is a triphenylphosphine metal catylst represented by the following general formula (I);

M(PPh₃)                    (I)

wherein M represents Dalladium.

4. The method of claim 1, wherein the polymer that has side chains containing an aromatic substituent is a polymer having styrene units.

5. The method of claim 3, wherein the polymer that has side chains containing an aromatic substituent is a polymer having styrene units.

* * * * *